United States Patent
Powers et al.

[11] Patent Number: 5,879,374
[45] Date of Patent: Mar. 9, 1999

[54] EXTERNAL DEFIBRILLATOR WITH AUTOMATIC SELF-TESTING PRIOR TO USE

[75] Inventors: Daniel J. Powers, Bainbridge Island; David Cameron; Clinton S. Cole, both of Seattle; Thomas D. Lyster; Steven T. Mydynski, both of Bothell; Carlton B. Morgan, Bainbridge Island, all of Wash.

[73] Assignee: Heartstream, Inc., Seattle, Wash.

[21] Appl. No.: 240,272

[22] Filed: May 10, 1994

Related U.S. Application Data

[63] Continuation-in-part of Ser. No. 63,631, May 18, 1993, abandoned.

[51] Int. Cl.⁶ .................................................. A61N 1/39
[52] U.S. Cl. ............................................................ 607/5
[58] Field of Search ............................. 607/4, 5, 3, 6–8; 324/403, 415, 500, 512, 519, 523, 525, 527; 330/2

[56] References Cited

U.S. PATENT DOCUMENTS

| | | |
|---|---|---|
| 3,747,605 | 7/1973 | Cook . |
| 3,983,476 | 9/1976 | Konopasek . |
| 4,164,946 | 8/1979 | Langer . |
| 4,407,288 | 10/1983 | Langer et al. . |
| 4,488,555 | 12/1984 | Imaran ........................................ 607/9 |
| 4,504,773 | 3/1985 | Suzuki et al. . |
| 4,595,009 | 6/1986 | Leinders . |
| 4,610,254 | 9/1986 | Morgan et al. . |
| 4,625,730 | 12/1986 | Fountain et al. . |
| 4,628,935 | 12/1986 | Jones et al. . |
| 4,745,923 | 5/1988 | Winstrom . |
| 4,771,781 | 9/1988 | Leman ........................................ 607/8 |
| 4,785,812 | 11/1988 | Phil ............................................. 607/8 |
| 5,078,134 | 1/1992 | Heilman et al. . |
| 5,080,099 | 1/1992 | Way et al. . |
| 5,097,830 | 3/1992 | Eikefjord et al. ........................... 607/8 |
| 5,099,844 | 3/1992 | Faupel . |
| 5,201,865 | 4/1993 | Kuehn ........................................ 607/9 |
| 5,222,492 | 6/1993 | Morgan et al. . |
| 5,224,870 | 7/1993 | Weaver et al. ............................. 607/5 |
| 5,231,987 | 8/1993 | Robson . |
| 5,249,573 | 10/1993 | Fincke et al. . |
| 5,285,792 | 2/1994 | Sjoquist et al. ............................ 607/5 |
| 5,402,884 | 4/1995 | Gilman et al ............................ 206/328 |

FOREIGN PATENT DOCUMENTS

| | | |
|---|---|---|
| 0 327 304 | 8/1989 | European Pat. Off. . |
| 0472411 A1 | 2/1992 | European Pat. Off. . |
| 0551746 A2 | 7/1993 | European Pat. Off. . |
| 2172681 A | 9/1973 | France . |
| 2712352 A1 | 9/1978 | Germany . |
| 93/16759 | 8/1993 | WIPO . |

OTHER PUBLICATIONS

Stratbucker et al "Rocky Mountain Engineering Society", 1965, pp. 57–61.

Lagrdal Publication No. 903703/10003506 Rev. X Sep. 1992, 22 pp.

Spacelabs Medical Publication No. 5M06102990, Dec, 1992, 3 pp.

Product Brochure from "Vivalink AED Automatic External Defibrillator System" by Survivalink Corporation. 2975 84th Lane NE, Minneapolis, MN, 55449, 4 pages total.

*Primary Examiner*—William E. Kamm
*Attorney, Agent, or Firm*—James R. Shay; Cecily Anne Snyder

[57] ABSTRACT

A defibrillator with an automatic self-test system that includes a test signal generator and a defibrillator status indicator. The test system preferably performs functional tests and calibration verification tests automatically in response to test signals generated periodically and/or in response to predetermined conditions or events and indicates the test results visually and audibly. The invention also relates to a method for automatically determining and indicating a defibrillator's status without human intervention.

73 Claims, 7 Drawing Sheets

| TEST DESCRIPTION | BIT | WPST | MPST | DPST | POST | RUN TIME |
|---|---|---|---|---|---|---|
| CPU SELF-TEST | X | X | X | X | X | |
| SYSTEM GATE ARRAY | X | X | X | X | X | |
| SYSTEM MONITOR GATE ARRAY | X | X | X | X | X | |
| PROGRAM ROM CRC | X | X | X | X | X | |
| SYSTEM RAM CHECKSUM | X | X | X | X | X | |
| VIDEO RAM CHECKSUM | X | X | X | | | |
| DEVICE FLASH ROM CHECKSUM | X | X | X | | | |
| SYSTEM WATCH DOG | X | X | X | X | X | X |
| PCMCIA CARD VERIFY | X | | | | | |
| | | | | | | |
| FRONT END GAIN | X | X | X | X | | |
| ARTIFACT SYSTEM | X | X | X | X | | |
| CMR CHANNEL | X | X | X | X | | |
| DEFIBRILLATOR CONN/RELAY | X | X | X | X | | |
| | | | | | | |
| BATTERY SENSE CELL MEASUREMENT | X | X | X | X | X | X |
| BATTERY SENSE CELL LOAD MEASUREMENT | X | X | X | X | X | X |
| BATTERY STACK LOAD CHECK | X | X | X | X | X | X |
| POWER SUPPLIES CHECK | X | X | X | X | X | X |
| | | | | | | |
| HV ISOLATION RELAY | X | X | X | | | |
| HIGH VOLTAGE DELIVERY SUBSYSTEM | X | X | X | | | |
| WAVEFORM DELIVERY | | | | | | X |
| | | | | | | |
| CALIBRATION STD. VOLTAGE | X | X | X | X | X | X |
| CALIBRATION STD. TIME | X | X | X | X | X | X |
| CALIBRATION STD. RESISTANCE | X | X | X | X | | |
| | | | | | | |
| STUCK BUTTON TEST | X | X | X | X | | |
| BUTTON TEST | X | | | | | |
| LIGHT ALL LED'S | X | | | | X | |
| LCD TEST PATTERN | X | | | | | |
| LCD BACKLIGHT VERIFY | X | | | | | |
| SPEAKER OUTPUT TEST | X | | | | X | |
| PIEZO BEEPER TEST | X | | | | X | |

FIG. 6

FIG. 8 ns and opera- 20 respect to the drawings.

EXTERNAL DEFIBRILLATOR WITH AUTOMATIC SELF-TESTING PRIOR TO USE

CROSS REFERENCE TO RELATED APPLICATION

This application is a continuation-in-part of U.S. patent application Ser. No. 08/063,631, filed May 18, 1993, now abandoned the disclosure of which is incorporated herein by reference.

BACKGROUND OF THE INVENTION

This invention relates generally to a defibrillator system that performs periodic self-tests and, in particular, to a method and apparatus for performing periodic functional, calibration and safety tests in an automatic external defibrillator to verify that the defibrillator's components and operation are within preset specifications.

Prior art external defibrillators were used primarily in the hospital. In that environment, the frequency with which a particular defibrillator was used was relatively high, e.g., on the order of several times per week. Periodic verification tests for these prior art defibrillators typically amounted to a battery level test and a functional test in which the defibrillator was hooked to a test load and discharged. These tests were usually performed once per day or once per shift per manufacturer recommendations. Other tests, such as recalibration of internal circuit components by a biomedical technician, were performed less often, on the order of twice per year, also pursuant to manufacturer recommendations. Each of these maintenance tests for prior art defibrillators was initiated and performed by human operators.

SUMMARY OF THE INVENTION

While adequate for relatively frequently-used hospital-based defibrillators, prior art defibrillator test apparatuses and procedures are not optimal for use with portable defibrillators that are used less frequently. For example, defibrillators carried by emergency medical vehicles might need to be used only on a monthly basis. The burden of performing manual battery and performance tests on a daily basis could outweigh the benefits of carrying the infrequently-used defibrillator on the vehicle. The tests should therefore be performed by the defibrillator automatically.

Because the tests are performed automatically, the tests should be both accurate and reliable. The portable defibrillator's mobile environment could add to the frequency of defibrillator component failure, thus increasing the need for periodic tests. In addition, portable defibrillators could be exposed to environmental conditions (such as severe vibration, sudden impacts, heat or moisture) that require an immediate reevaluation of a defibrillator's operational status.

Also, the nature of the tests performed should be different in the portable defibrillator environment because of the relatively infrequent use of the defibrillators. Deterioration of system components over time could move the defibrillator out of its originally specified operating parameters. An infrequently used defibrillator should provide an operator with an indication not only of whether it will operate at all but also verify that the defibrillator meets its established specifications.

Defibrillators are used in emergency situations in which time is of the essence. The operational status of a particular defibrillator as determined by the self-tests should be therefore readily apparent to an operator.

Finally, there is a need for a defibrillator that can automatically recalibrate itself if certain of its system components drift from their initial values. This automatic recalibration minimizes the burden on the defibrillator's operator or maintainer and lengthens the defibrillator's useful life.

This invention is a defibrillator with an automatic self-test system that includes a test signal generator and a defibrillator status indicator. The test system preferably performs functional tests and calibration verification tests automatically in response to test signals generated periodically and/or in response to predetermined conditions or events and indicates the test results visually and audibly. The invention also relates to a method for automatically determining and indicating a defibrillator's status without human intervention.

The invention is described in more detail below with respect to the drawings.

DETAILED DESCRIPTION OF THE PREFERRED EMBODIMENT

This invention is a method and apparatus for automatically determining the status of a defibrillator, for displaying that status to a user or operator, and, for recalibrating certain defibrillator components. The invention is particularly useful for increasing the reliability of infrequently-used defibrillators by providing an indication of a defibrillator's operational status and by recalibrating the defibrillator, where possible, prior to any attempted use of the defibrillator.

In a preferred embodiment, the defibrillator automatically generates a test signal either (1) periodically in response to the passage of time or (2) in response to a specified event or condition, such as the insertion of a new battery or a manual power-up command from an operator. The test signal initiates a plurality of preset self-tests within the defibrillator. The self-tests may include functional tests that verify the operation of certain defibrillator components and subsystems. The self-tests may also include calibration verification tests that determine whether certain defibrillator components and subsystems are operating at preset specifications or within preset specification ranges. In addition, the defibrillator may automatically recalibrate certain components or subsystems in response to a calibration verification test.

No matter what test or collection of automatic self-tests the defibrillator performs, the defibrillator indicates its operational status as determined by the self-tests, such as through a visual display. The indication is preferably fail-safe so that a failure of the status indication mechanism itself will result in the indication of an inoperable defibrillator status.

Figure 1:
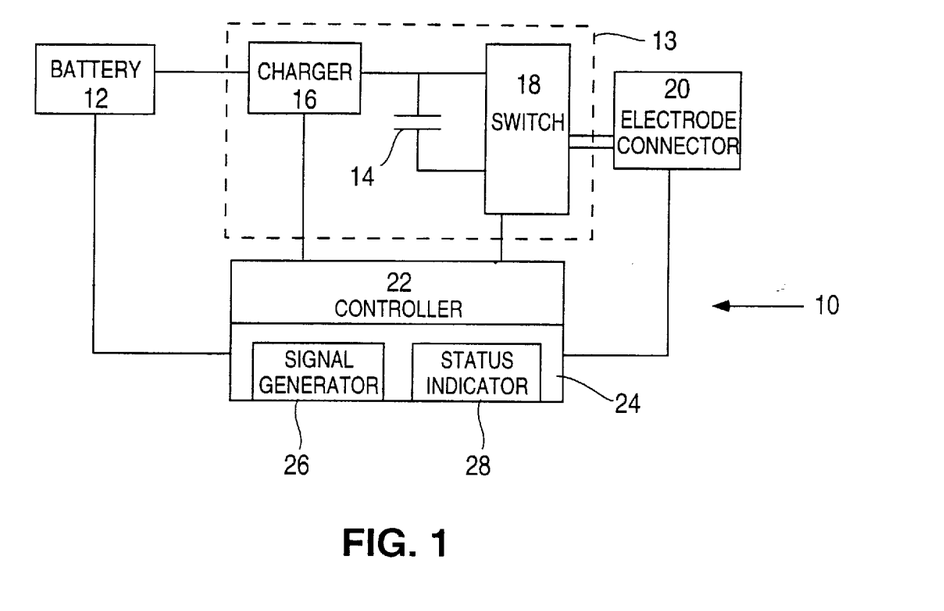
FIG. 1 is a block diagram showing a defibrillator according to this invention.

FIG. 1 is a schematic representation of a defibrillator constructed and operated according to this invention. The defibrillator 10 includes a battery 12, a high voltage delivery system 13 (preferably consisting of a capacitor or capacitor bank 14, a capacitor charger 16 and a switching mechanism 18), an electrode connector 20 and a controller 22 that operates the charger and switching mechanism to deliver an electric shock from the capacitor to electrodes connected to the electrode connector or interface 20. The defibrillator has a testing system 24 including a test signal generator 26 and a defibrillator status indicator 28. The purpose of testing system 24 is to test the operational status of the defibrillator's components and to provide an indication of that status automatically in response to predetermined events or conditions and/or periodically on a preset schedule.

While the testing system 24 and controller 22 are shown in FIG. 1 as separate elements, they could be combined into a single element that performs all testing and operational control functions. In addition, the testing system 24 may also include components located within other defibrillator subsystems, such as within the high voltage delivery system. In any event, the testing system communicates with the tested defibrillator components and systems via communication channels to control the tests and to gather information about the status of the tested components. The testing system also communicates indicator control signals to the status indicator via communication channels as well.

Figure 2:
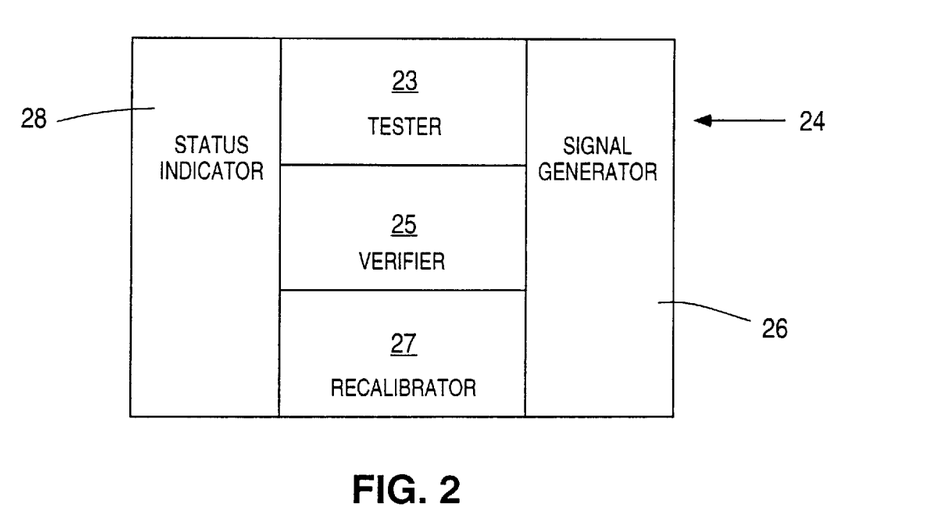
FIG. 2 is a schematic diagram showing a testing system of a defibrillator according to this invention.

FIG. 2 is a schematic drawing showing self-testing subsystems making up testing system 24 in the preferred embodiment. It is not necessary that a given defibrillator include each of the subsystems shown in FIG. 2. According to this invention, the defibrillator must include at least one automatic self-test that is initiated in response to a test signal generated either periodically or as a result of a specified event or condition.

Also, it is not necessary for the apparatus performing each test in each subsystem to be in the same physical location. FIG. 2 is a logical grouping and is not intended to be an actual drawing of a defibrillator or defibrillator subsystem.

Each self-test in each group of FIG. 2 responds to a test initiation signal from signal generator 26, and the result of each self-test in each group affects the status is indicated on status indicator 28. This collection of self-testing subsystems may be added to or subtracted from without departing from the invention. In addition, while there may be other tests performed by the defibrillator that do not meet these criteria, such tests form no part of this invention.

The first testing subsystem is the functionality tester 23. The self-tests performed by this subsystem test the operability and functionality of defibrillator components and/or subsystems. Examples include the testing of switches within the switching mechanism of the high voltage delivery system and the testing of registers within the defibrillator's controller.

The second testing subsystem is the calibration verifier 25. The self-tests performed by this subsystem determine whether certain defibrillator components and/or subsystems meet preset specifications. Examples include determining the capacitance of the defibrillator's capacitor and checking the response of the controller to capacitor voltage values.

The testing system also may include a recalibrator 27 that adjusts a component or subsystem of the defibrillator in response to a determination that the component or subsystem is no longer, or no longer operates, at a specified value or within a specified range of values. For example, parameters used by the defibrillator's controller to control operation of the high voltage delivery system may be changed to reflect changes in the values of defibrillator components.

The actual self-tests automatically performed by a defibrillator's testing system depend in part on the defibrillator's structure and in part on reliability goals set by the defibrillator's designer. Trade-offs may be made between the completeness of a given self-test (which adds to the reliability of the defibrillator product) and the cost of implementing a complete and accurate self-test. A particular implementation of a defibrillator and its self-testing system is described below. The discussion merely illustrates a preferred embodiment of the invention. Our invention covers other defibrillator designs and other collections of defibrillator self-tests as well.

Figure 3:
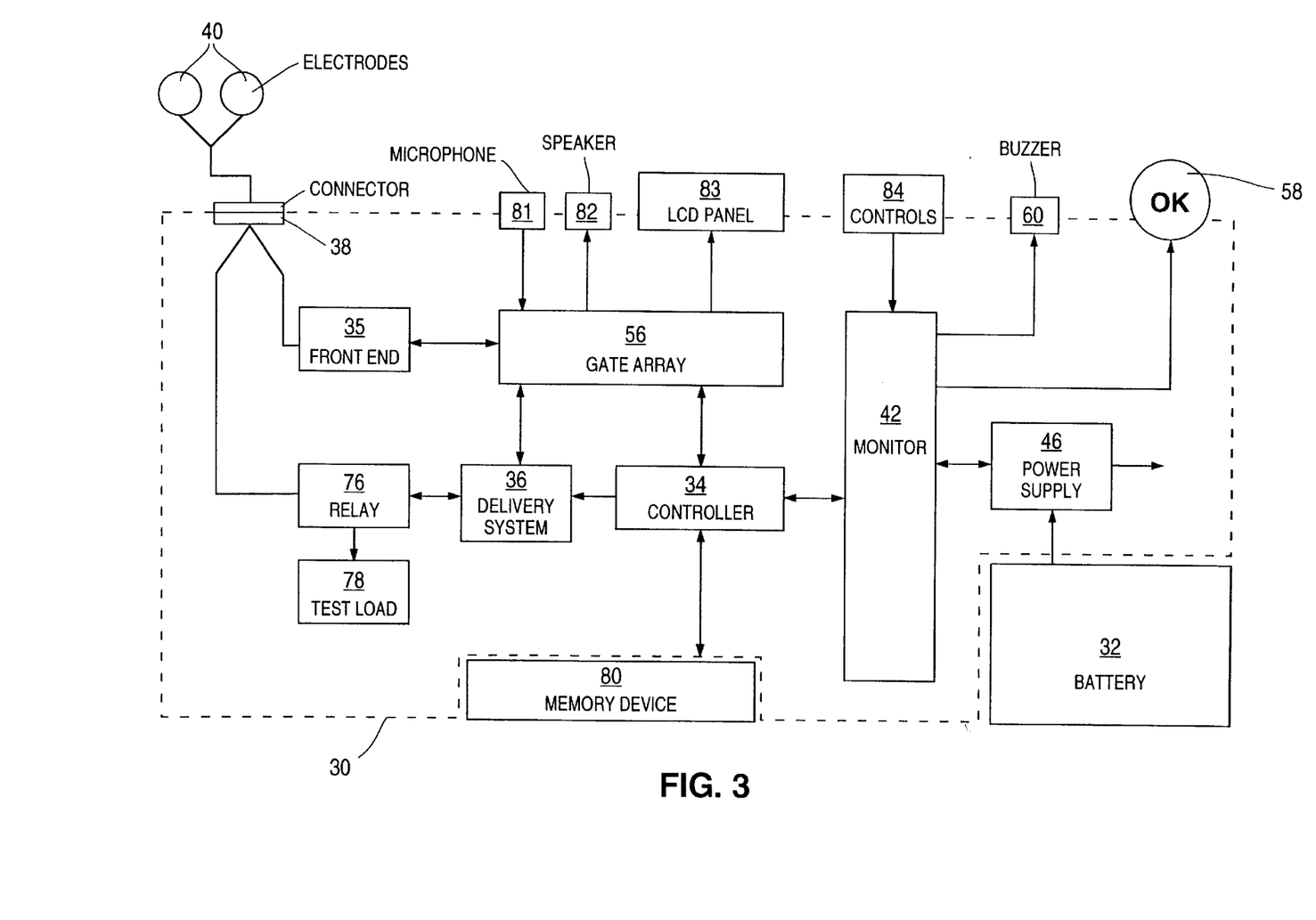
FIG. 3 is a block diagram showing some of the components of an external defibrillator according to a preferred embodiment of this invention.

FIG. 3 is a block diagram showing a preferred configuration for the defibrillator of this invention. Some of the elements are described in more detail further below. Defibrillator elements not specifically described in this application may be configured and operated in the manner described in U.S. patent application Ser. No. 08/227,553, now U.S. Pat. No. 5,607,454 "Electrotherapy Method and Apparatus," filed Apr. 14, 1994, the disclosure of which is incorporated herein by reference.

As shown in FIG. 3, external defibrillator 30 has a power source such as a removable battery 32, a controller such as CPU 34, and a high voltage delivery system 36 including a capacitor or capacitor bank and appropriate switches (not shown) to deliver a pulse of electrical energy to an electrode connector or interface 38 and then to a patient via electrodes 40. Delivery of the electrical pulse is controlled by CPU 34. A test and isolation relay 76 and a test load 78 are provided for reasons explained below.

An ECG front end system 35 acquires and preprocesses the patient's ECG signals through electrodes 40 and sends the signals to CPU 34 via a system gate array 56. System gate array 56 is a custom application specific integrated circuit (ASIC) that integrates many of the defibrillator's functions, such as display control and many of the instrument control functions, thereby minimizing the number of parts and freeing up main CPU time for use in other tasks. The system gate array could be replaced by discrete logic and/or another CPU, of course, as known in the art.

The external defibrillator shown in FIG. 3 also has a memory device 80 (such as a removable PCMCIA card or a magnetic tape), a microphone 81, a speaker 82, a LCD panel 83 and a set of illuminated push-button controls 84. None of these elements is critical to the present invention.

A system monitor mediates the external defibrillator's self-testing functions by watching for scheduled test times and unscheduled power-on events. The system monitor generates test signals periodically at scheduled times and in response to specified events. The system monitor is also responsible for operating a fail-safe defibrillator status indicator or display. The system monitor communicates test signals to the CPU via a communication channel, and the CPU controls and gathers information from tested defibrillator components via other communication channels, some of which pass through system gate array 56.

In the embodiment shown in FIG. 3, system monitor 42 is separate from CPU 34 so that power can be provided to the system monitor without powering any other part of the defibrillator. Thus, system monitor 42 has its own power supply 44 apart from the defibrillator power supply 46, as shown more specifically in FIG. 4. This dedicated power supply 44 draws approximately 30 microamps from battery 32 and is active whenever power is available from the battery. The dedicated system monitor power supply may also have its own battery apart from the main battery.

Figure 4:
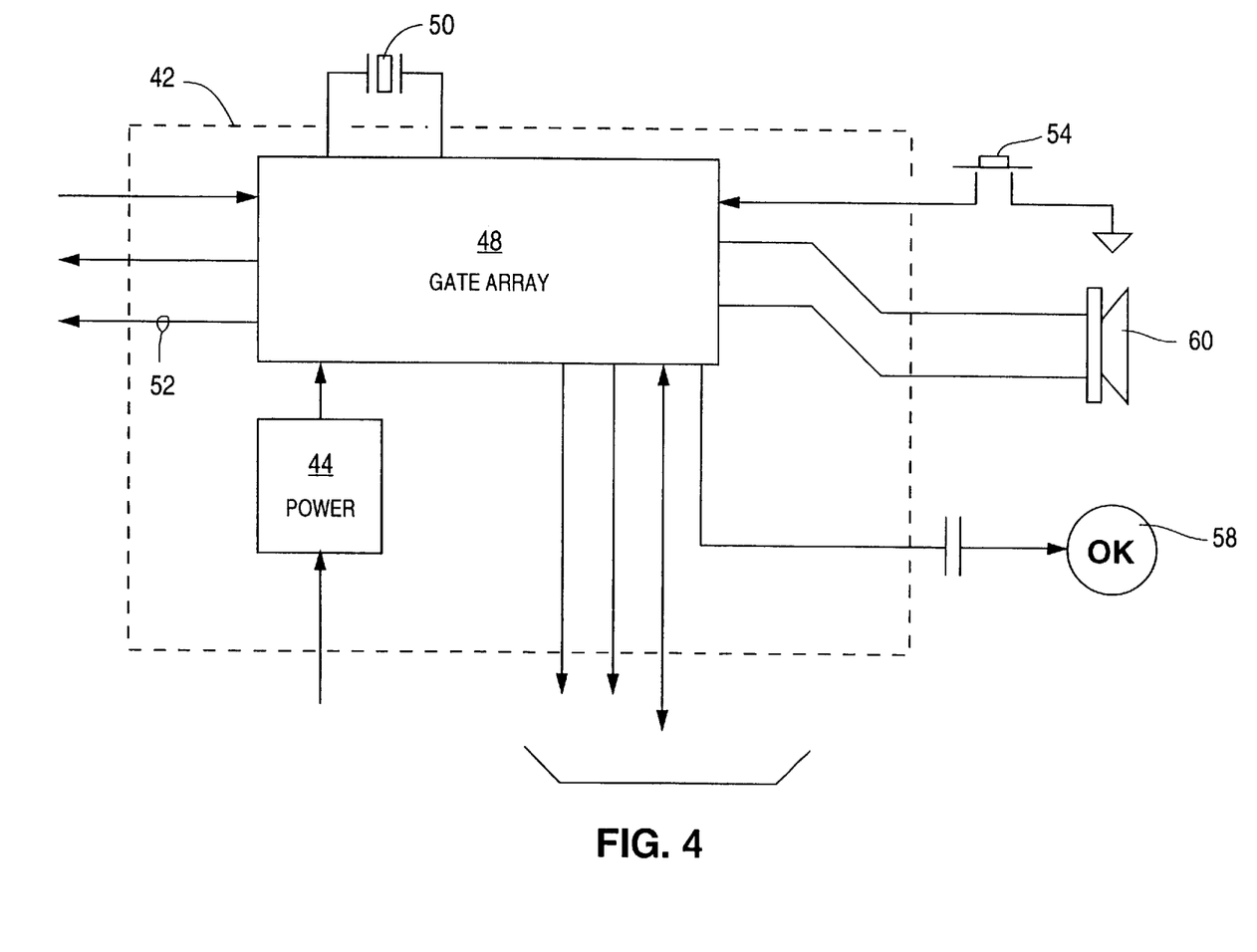
FIG. 4 is a block diagram showing the system monitor of the embodiment of FIG. 3.
Figure 5A:
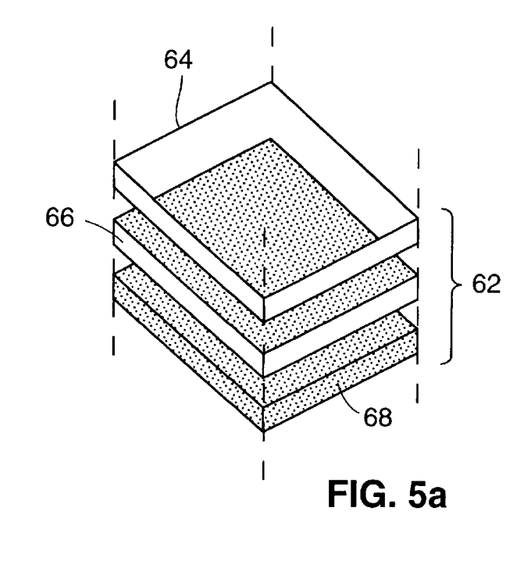
FIG. 5, parts (a)–(e) shows various aspects of a visual display according to the embodiment of FIG. 3.
Figure 5B:
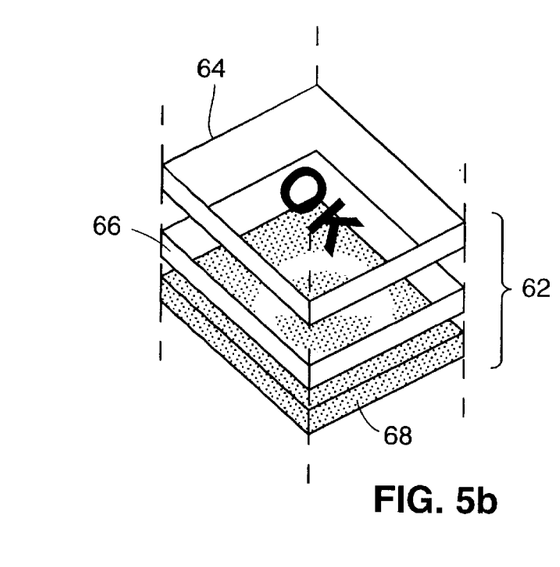
Figure 5C:
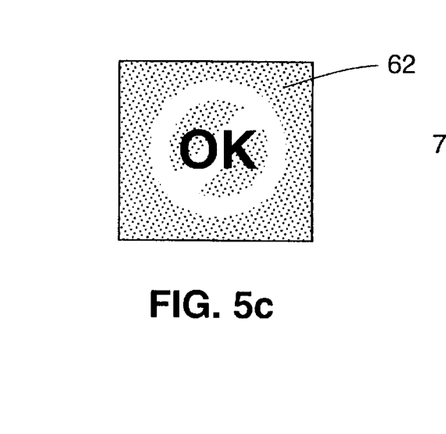
Figure 5D:
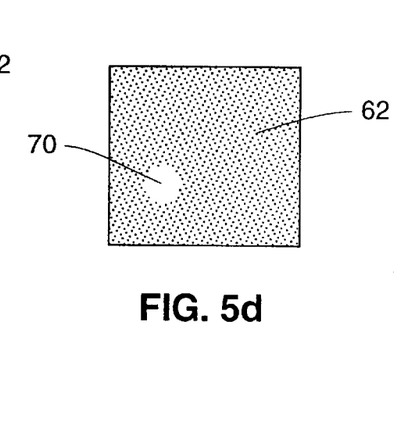
Figure 5E:
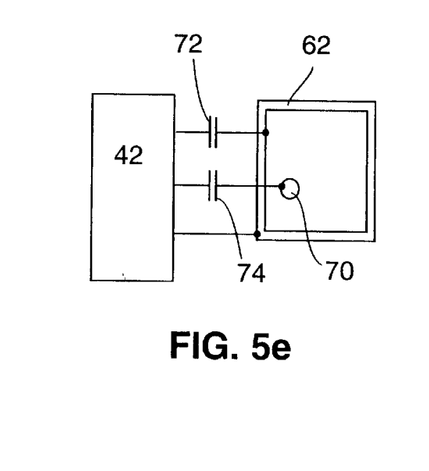

As shown in more detail in FIG. 4, the other major element of system monitor 42 is a low-power gate array 48. In this preferred implementation, gate array 48 is a 44-pin custom ASIC. Gate array 48 is preprogrammed to perform the functions of the system monitor. As an alternative, the system monitor could be implemented with a low power CPU and/or with discrete logic components.

Gate array 48 operates a 32.768 kHz crystal oscillator to provide the defibrillator testing system's scheduling function. The gate array divides the oscillator's frequency repeatedly to generate periodic (e.g., daily, weekly, monthly) test initiation signals. The system monitor also sends a 32.768 kHz clock signal out on line 52 to be used by the defibrillator system to perform other functions.

In addition to the periodic tests, certain defibrillator self-tests are performed rapidly in response to activation of the defibrillator's ON button (shown schematically as element 54 in FIG. 4) by an operator. Activation of the ON button 54 prompts the system monitor to generate a power-on test initiation signal.

The system monitor indicates the status of the defibrillator as a result of the periodic and power-on self-tests. The status indicator should be fail-safe so that the indicator will indicate an inoperable status if the system monitor should fail. The system monitor communicates control information to the status indicator through communication channels.

In a preferred embodiment, the system monitor 42 powers a status indicator consisting of a visual display 58 and a piezo buzzer 60 to indicate the operational status of the defibrillator to a user. As shown in more detail in FIG. 5, visual display 58 may be a multiple-part LCD 62 powered by the system monitor via AC-coupled drive 72. The top plate 64 of the LCD is a clear window with an "OK" symbol printed on its back. The middle plate 66 is an LCD shutter that is biased so as to be opaque when driven by the system monitor via drive 72. The bottom plate 68 has an international "Not" symbol on its top surface. Middle plate 66 also includes a separately addressable portion 70 driven by the system monitor via AC-coupled drive 74.

In operation, the system monitor 42 drives LCD shutter 66 only when confirmation of successful testing is received within an expected time window. The visual display would then appear as in FIG. 5, part (*d*). Failure to receive proper test confirmation within the allotted time window will cause the system monitor to cease issuing drive signals to shutter 66. Shutter 66 will then go transparent to superimpose an international "Not" symbol on the "OK" symbol in the LCD as shown in FIG. 5, part (*c*). The system monitor will also then begin powering a piezoelectric failure alert buzzer 60, preferably for 200 msec, every 10 sec, so long as there is power enough to do so.

The primary advantages of the visual display of the preferred embodiment are its low power requirements and the fact that it is powered by an AC signal rather than a DC signal. This latter point ensures the display's fail-safe nature, since the shutter of middle plate 66 cannot be maintained opaque without the active involvement of the system monitor generating the AC signal.

Separately addressable portion 70 serves as a positive indication (in addition to the fail-safe "OK" symbol) that the defibrillator has power and is functioning properly. Portion 70 blinks periodically through the alternating driving and releasing of the signal to portion 70 through drive 74.

In an alternative embodiment, an LCD shutter covering an "OK" symbol is driven open to display the "OK" symbol to indicate an operational defibrillator status. The shutter is permitted to close to cover the "OK" symbol to indicate that the defibrillator is not operational. Another alternative category of fail-safe indicators include electromechanical devices, such as those used for aircraft instrumentation.

In response to the generation of a test initiation signal, the system monitor commands the defibrillator's power system to turn on. The CPU then issues an appropriate series of commands to perform the required tests. The tests performed in response to the periodic and power-on test initiation signals are described in more detail further below with reference to the table shown in FIG. 6.

Figure 6:
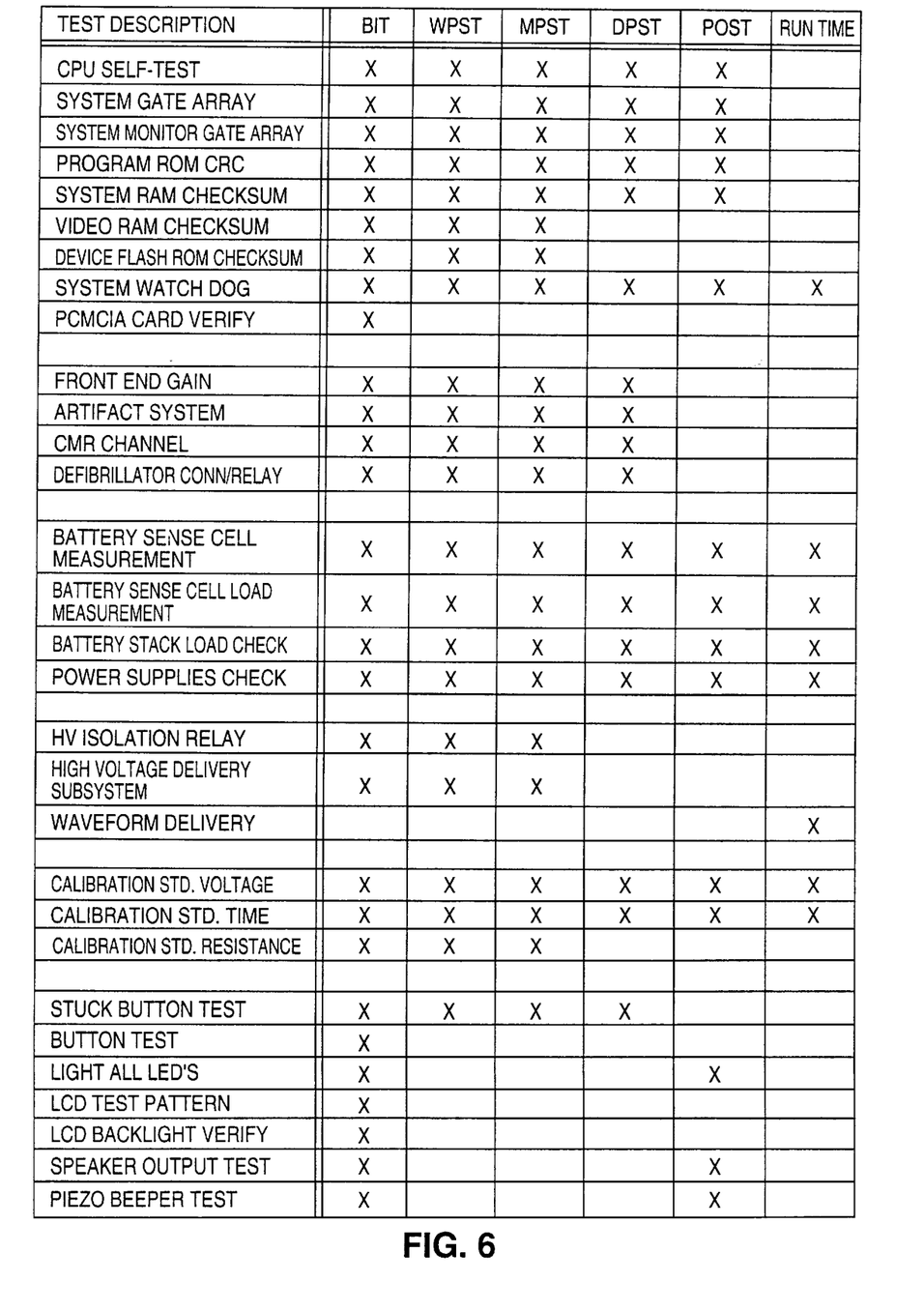
FIG. 6 is a table showing groupings of external defibrillator self-tests according to a preferred embodiment of this invention.

FIG. 6 shows the scheduling of some of the tests that can be performed by the self-test system of this invention. Some of the tests are performed when a battery is inserted, some are performed daily, some are performed weekly, some are performed monthly, some are performed when an operator powers-up the external defibrillator, and some are performed during operation of the defibrillator. FIG. 6 is not an exhaustive list of possible tests, nor is performance of any particular test listed in FIG. 6 essential to the invention. The tests and test groupings shown in FIG. 6 are merely an example illustrating this invention.

The first test grouping is the Battery Insertion Test or BIT. The BIT tests all internal subsystems, allows the user to verify PCMCIA card type, setup parameters, and the proper operation of systems that are only externally observable (e.g., LCD operation and button functionality). The BIT is performed whenever a good battery is inserted into the defibrillator, unless the defibrillator's electrodes are attached to a patient.

The second test grouping shown in FIG. 6 is the Monthly Periodic Self-Test (MPST). The MPST performs the same automated tests as the BIT, but in order to conserve power it does not run the externally observable systems (e.g., LCD, LED's, etc.). The MPST is performed once every 28 days so long as a good battery is maintained in the defibrillator.

The third test grouping shown in FIG. 6 is the Weekly Periodic Self-Test (WPST). The WPST performs essentially the same automated tests as the MPST, except the test shock is not performed in order to conserve power. The WPST is performed once every 7 days so long as a good battery is maintained in the defibrillator.

The fourth test grouping shown in FIG. 6 is the Daily Periodic Self-Test (DPST). The DPST performs fewer tests than the WPST in order to conserve power.

The fifth test grouping shown in FIG. 6 is the Power-On Self-Test (POST). The POST is performed whenever an operator turns the defibrillator from OFF to ON in preparation for use of the defibrillator on a patient. The tests performed in the POST are selected to provide the highest confidence of instrument functionality in the shortest possible time.

The final grouping of tests in FIG. 6 is the Runtime Tests. These tests are performed continually during runtime to assess the safety and effectiveness of portions of the defibrillator. The tests are explained in more detail below.

The self-tests listed in FIG. 6 are not necessarily listed in the order performed. The performance order depends in part on the interrelationship of the components and functions tested. To the extent there is no such relationship, then the self-test order is arbitrary.

In general, failure of a self-test results in an indication of an inoperable status or error status by the defibrillator's status indicator. For example, in the defibrillator described above, failure of a self-test would result in the display of the "Not OK" symbol by the system monitor and activation of the audible failure signal. The system monitor takes this action if it receives a signal from the CPU or from the system gate array that a test has failed (i.e., that a tested component is not functional or that the component's calibration could not be verified) or if the system monitor does not receive information showing that the currently-scheduled self-test has passed before the expiration of the watchdog's time-out period (e.g., 200 msec.).

In a preferred embodiment of this invention, self-test scheduling and result information may be stored in system memory for later diagnosis of the defibrillator by a technician or operator. For example, in the defibrillator described above, date and time information regarding the self-tests performed are stored in internal memory and/or in the removable memory 80 (e.g., PCMCIA card) so that a history of performed tests can be obtained by a technician or operator. In addition, if a self-test indicates that a component or subsystem is not functional or is out of calibration, or if any recalibration has been performed, detailed information about that test is stored in internal memory and/or in removable memory. Information regarding environmental conditions (temperature, humidity, moisture, impacts) may also be stored for use in later diagnosis.

The CPU self-test is a functional test. During the CPU self-test the CPU tests its internal register integrity and verifies its access to local and external memory locations. If the CPU does not pass these initial tests, it attempts to notify the user of a system failure by writing to a system failure register in the system monitor, resulting in a status display showing "Not OK". If the CPU does not respond to the system monitor within 200 msec of power on, the system monitor assumes the CPU is dead, and the "Not OK" symbol is displayed.

The System Gate Array self-test is also a functional test. In the System Gate Array self-test, the CPU verifies that it can write to and read from the system gate array register set. This test also tests other components of the system gate array, such as whether defibrillator waveform control state machines are functioning correctly. Test failures are handled as for the CPU self-test above.

The System Monitor Gate Array self-test is a functional test as well. The System Monitor Gate Array self-test verifies that the CPU can write to and read from the system monitor.

At the beginning of the Program ROM CRC (Cyclic Redundancy Check) self-test, the CPU resets the system monitor watchdog and executes a CRC on program ROM. This test is a functional test.

In the System RAM Checksum self-test (a functional test), RAM used for data memory is verified using a test pattern that has a high probability of identifying both address and data faults within RAM. Once the pattern has been written to system RAM, the test calculates a checksum based on the system RAM contents.

In the Video RAM Checksum self-test, RAM used for video memory is verified in the same manner as for the system RAM. This self-test is a functional test.

In the Device Flash ROM Checksum self-test, a checksum of the voice data pointer and voice data record is calculated and compared with the checksum value stored in the internal flash ROM. This self-test is a functional test as well.

In the System Watchdog Verify self-test, the CPU verifies the watchdog by writing a known watchdog time-out into the watchdog register and looping until the watchdog time-out register in the system monitor indicates that the watchdog timer has expired. During this test, the watchdog outputs, NMI, and RESET are disabled. The CPU signals a failure if the watchdog timer does not expire within the expected time frame.

The PCMCIA Card Verify self-test is a functional test that checks for the presence and type of the removable memory.

The next four self-tests listed in FIG. 6—Front End Gain, Artifact System, CMR Channel, and Defibrillator Connector/Relay—are all part of the ECG front end tests. These tests verify the functionality and verify the calibration of the ECG input circuitry and the patient/electrode connection circuitry. These tests are not performed during the POST since the tests assume that there is no load attached to the defibrillator output connector.

Figure 7:
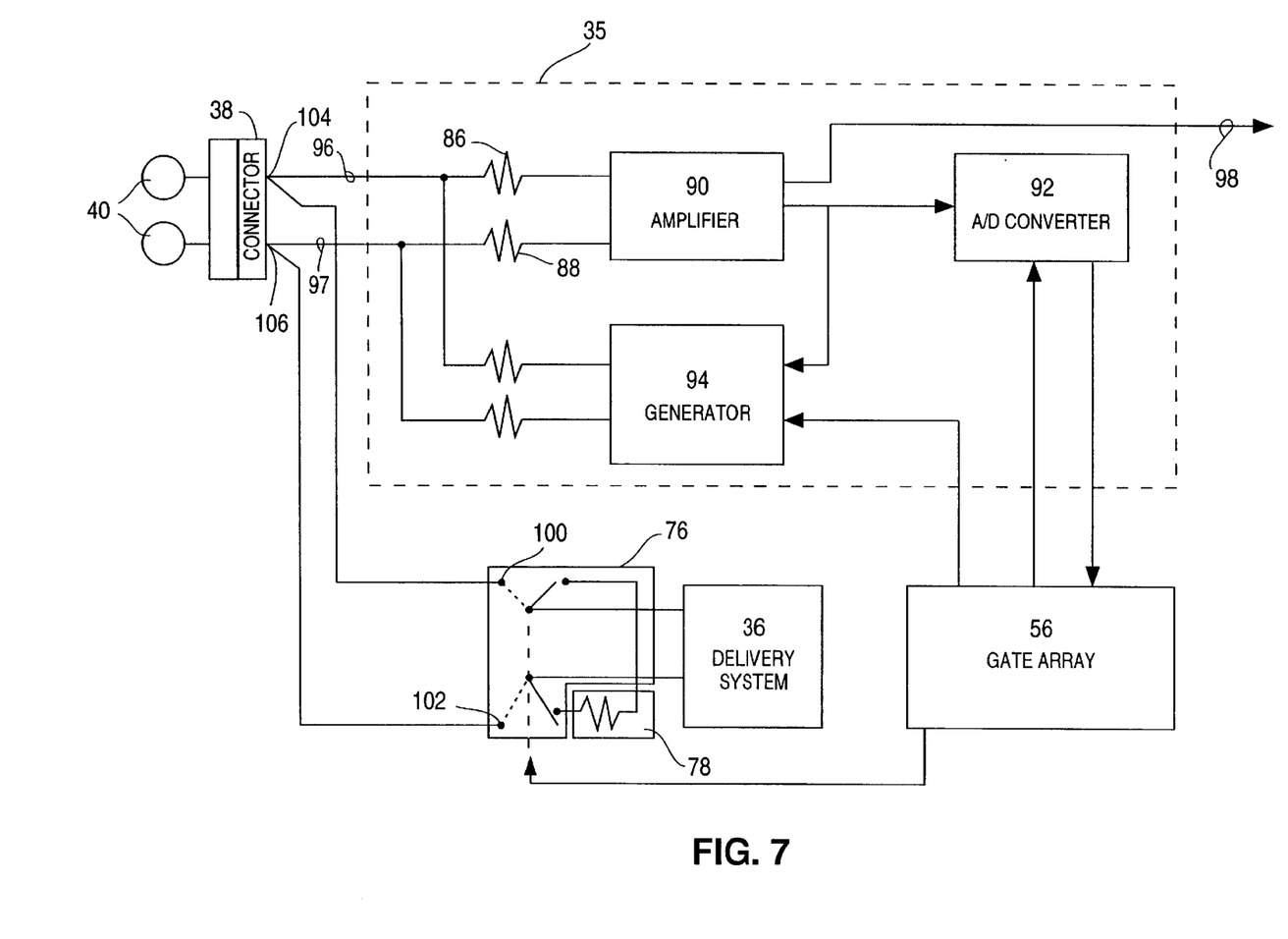
FIG. 7 is a block diagram showing the interaction of an ECG front end and a testing system according to a preferred embodiment of this invention.

An explanation of some special features of the external defibrillator of this invention is required as background for the ECG front end tests. FIG. 7 shows the ECG front end 35 in relationship to the system gate array 56, the high voltage delivery system 36, a test and isolation relay 76 and the patient connector 38, as well as communication channels among some of these elements. The test and isolation relay 76 is normally in the state shown in FIG. 7 so that no shock can be delivered from the high voltage delivery system 36 to the patient connector 38 and to the electrodes 40 attached to a patient.

In this state, any signals from electrodes 40 will pass through a pair of protective resistors 86 and 88 to an ECG amplifier 90. A high resolution A/D convertor 92 digitizes the ECG data and sends it to the system gate array 56 for processing by the CPU to determine whether a shock is required. The system gate array 56 also sends control signals to the A/D convertor 92.

The ECG front end 35 also has a patient/electrode connection tester consisting of a signal generator 94 connected to the ECG signal input lines through a pair of protection resistors. The signal generator 94 receives input from the ECG analog output and carrier frequency commands from the gate array. The patient/electrode connection tester also produces an artifact test signal which is sent through ECG amplifier 90 to the CPU via line 98. ECG signal collection and analysis and artifact detection are not part of the present invention.

During automated testing, the system gate array 56 uses the signal generator 94 as a test signal injector to verify the function of the various ECG front end elements, wiring to the patient connector 38, and the normally-open contacts of the test and isolation relay 76. To test the ECG processing elements, the system gate array 56 causes the signal generator 94 to inject a small, low-frequency signal mimicking the amplitude and frequency characteristics of an ECG signal, thereby simulating a patient being monitored by the defibrillator. As the frequency of this test signal is varied, the digital data stream from the system gate array is checked by the CPU for values indicative of proper gain and filtering characteristics of the ECG front end, thus verifying the functionality and calibration of the analog and A/D conversion pathways.

In the Defibrillator Connector/Relay self-test, the function of the test and isolation relay contacts 100 and 102 and patient connector wiring are tested. The system gate array 56 causes the signal generator 94 to emit a 100 microamp, 600 Hz test signal and concurrently switches the test and isolation relay 76 to the normally-open position (shown in phantom in FIG. 7). The test current signal is carried to a 4-wire connection 104 and 106 directly on the patient connector contacts, through the relay common connection, and into the high voltage delivery subsystem 36, where both signal lines are held at ground potential. The relay 76 is then switched to its normally closed position. Carrier voltage is measured in both positions is indicative of the resistance of the circuit tested. When the relay is in normally open position, the carrier voltage should be approximately equal to the full scale voltage of signal generator 94. When the relay is in the normally closed position, carrier voltage should be approximately zero.

Finally, in the Artifact System self-test, the system gate array causes the signal generator 94 to emit signals indicative of artifact generation at the electrodes. Proper receipt of artifact signals of the expected amplitude at the CPU verifies the function and calibration of this channel.

There are three battery-related self-tests that are members of each of the test groupings in the preferred embodiment. The battery tests described below are based on a defibrillator design using the battery capacity indicator described in U.S. patent application Ser. No. 08/182,605, now U.S. Pat. No. 5,483,165 filed Jan. 14, 1994, (specifically, the embodiment of FIG. 2) the disclosure of which application is incorporated herein by reference. Other battery charge sensor arrangements and other battery charge subsystem self-tests may be used, of course, without departing from the scope of the invention.

The Battery Sense Cell Measurement self-test listed in FIG. 6 refers to a battery capacity test described in Ser. No. 08/182,605 now U.S. Pat. No. 5,483,165 in which a parameter of a single battery cell is monitored to determine the remaining capacity of the entire battery. In the preferred defibrillator configuration, this functional self-test determines whether the remaining battery capacity is sufficient for performing one more use of the defibrillator by determining whether the voltage of the sense battery cell is above a threshold value of approximately 2 volts. If not, then a Low Battery Warning State is entered. If this state is entered during a BIT, DPST, WPST or MPST, the unit returns to Stand-by mode displaying the "Not OK" symbol. If this state is entered during a POST or during runtime, the user is alerted by a symbol appearing on the LCD display 83 and with an audible prompt.

The second listed battery self-test is the Battery Sense Cell Load Check. This calibration verification self-test verifies the sense cell additional load circuitry described in Ser. No. 08/182,605 now U.S. Pat. No. 5,483,165 by turning the additional load circuitry on and off and measuring the voltage load across the load resistor. This test can actually be performed while performing the first battery self-test.

The third listed battery self-test is the Battery Stack Check. This functional test measures the voltage of the entire battery cell stack as a cross-check against the Battery Sense Cell Measurement test. If a portion of the battery stack other than the sense cell has been damaged, the voltage of the entire stack could be different than that which would have been expected based on the sense cell test.

In the Power Supplies Check calibration verification self-test, the system monitor activates the defibrillator's power supply system to supply power to all of the instrument's elements. Scaled representations of the voltages from the supplies are input for verification to the main CPU A/D convertor. For example, the major power supplies are: +18 volt switched battery; +5 volt for system monitor; +5 volts for main logic and analog; −5 volt for analog only; −14 to −22 volt CPU adjustable for LCD bias; +20 volts for IGBT switch drives; +2.5 volt reference for ECG front end; +5 volt reference for main CPU A/D convertor; and 50 ma current source supply for LCD backlight (tested by voltage developed). In addition, the high voltage supply is tested by its ability to charge the capacitor.

The HV Isolation Relay self-test determines the functionality of the test and isolation relay 76. In the first part of the test, the system gate array 56 moves the test and isolation relay to its normally open position, i.e., with the switches against contacts 100 and 102. The ECG front end measures the impedance across conductors 96 and 97. If the measured impedance corresponds to a predetermined impedance value, then the relay passes this part of the test.

The ECG front end then measures the impedance across conductors 96 and 97 with the test and isolation relay 76 in the normally closed position shown in FIG. 7. The measured impedance should be high (>14 k Ohms). If not, either a load is present at electrodes 40 or the relay failed to move completely to the normally closed position. In either case, the test fails, and the system monitor displays the "Not OK" symbol on the status indicator. In addition, failure to meet both parts of the Isolation Relay test prevents the defibrillator from performing the High Voltage Discharge Test described below.

Figure 8:
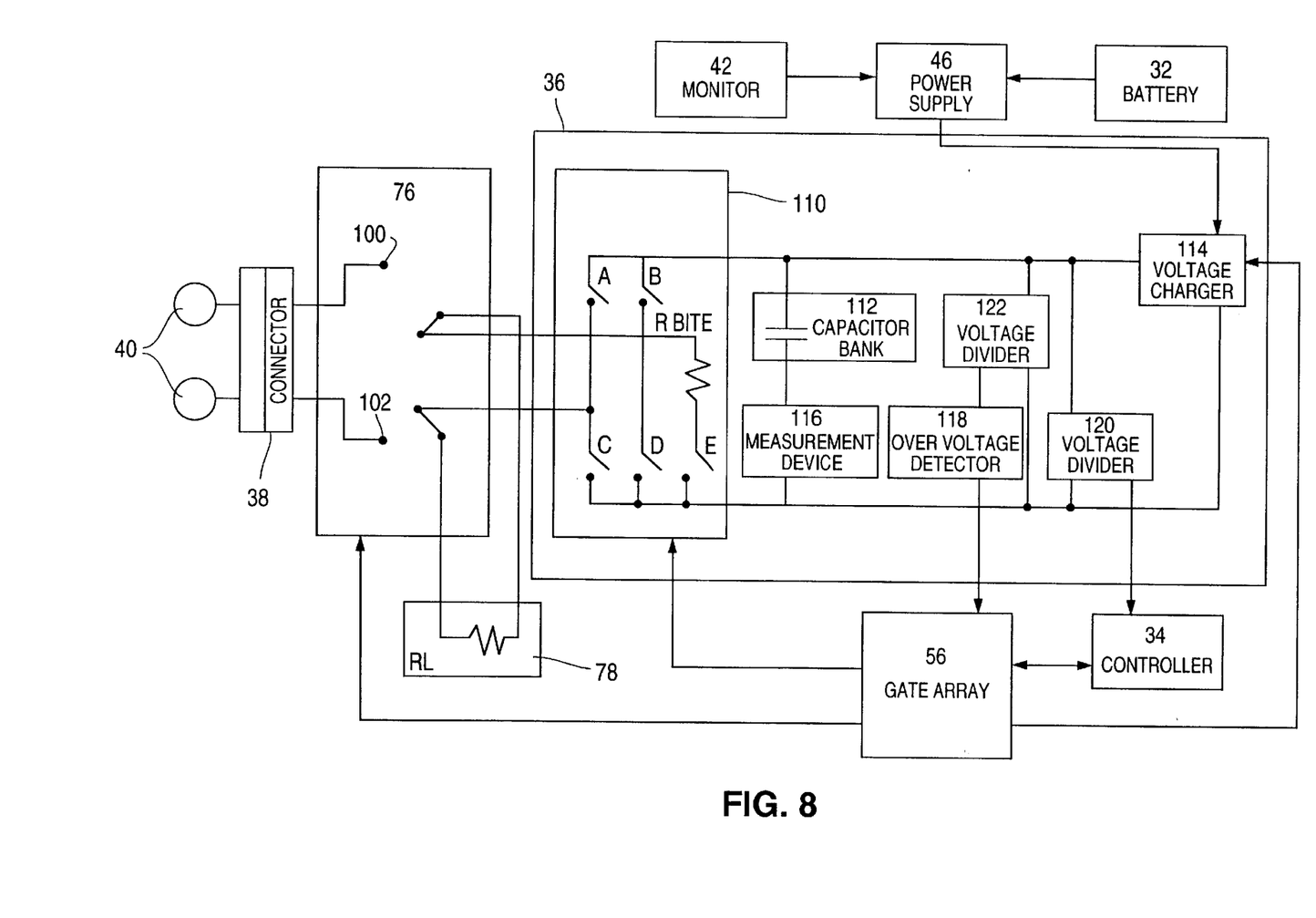
FIG. 8 is a block diagram showing the interaction of a high voltage delivery system and a testing system according to a preferred embodiment of this invention.

Under normal conditions, the defibrillator used to implement and practice the preferred embodiment of this invention delivers a biphasic waveform to the patient, as described in more detail in U.S. patent application Ser. No. 08/227,553 now U.S. Pat. No. 5,607,454. FIG. 8 provides further information regarding the preferred defibrillator's high voltage delivery system and how its operation is verified and calibrated during self-test.

High voltage delivery system 36 has a capacitor or capacitor bank 112 which can be charged to a preset voltage through a high voltage charger 114 connected to the power supply system 46 and battery 32. Operation of the high voltage charger is controlled by system gate array 56. A high voltage switch 110 consisting of five switches A–E and a shunt resistor $R_{BITE}$ controls delivery of the biphasic waveform from capacitor 112 to the patient connector 38 through test and isolation relay 76 under the control of system gate array 56.

Information regarding charge, current and voltage parameters at the capacitor is provided to system gate array 56 by a current and charge measurement device 116, an overvoltage detector 118 and a voltage divider 120. As described in more detail in Ser. No. 08/227,553 now U.S. Pat. No. 5,607,454, current and charge measurement device 116 is preferably a comparator that trips when a preset charge amount has been transferred from capacitor 112. The time required for this charge transfer is determined by system gate array 56 and is used to determine first and second phase durations via a look-up table in system gate array 56. All information and control signals pass among the elements via communication channels, some of which are shown schematically in FIG. 8.

As explained in Ser. No. 08/227,553 now U.S. Pat. No. 5,697,454, resistor $R_{BITE}$ is part of an overcurrent protection mechanism to protect circuit components from the effects of high current in the event that the impedance load between electrodes 40 is too low. Unless the initial current as measured by current and charge measurement device 116 is below a preset threshold, $R_{BITE}$ is kept in the waveform delivery circuit to limit the current flowing from capacitor 112 through the switching mechanism 110.

The high voltage delivery system has an overvoltage protector that protects switching circuit components from the effects of excessive voltage in the event of a higher than expected patient load resistance by preventing any transition from a first biphasic waveform phase to a second biphasic waveform phase. Analog voltage information from the capacitor is fed from a voltage divider 122 to an overvoltage detector 118. Overvoltage detector 118 is preferably a comparator that trips at a preset voltage. The status of the comparator is communicated to system gate array 56, which controls operation of the switching mechanism 110.

Finally, analog information regarding the charge state of capacitor 112 is sent to CPU 34 via voltage divider 120, where it is converted to digital form. This capacitor voltage information is used by the CPU to control capacitor charging.

The High Voltage Delivery Subsystem self-test actually includes a number of individual self-tests. Capacitor 112 is charged to full voltage (e.g., approx. 1710 volts). As the capacitor voltage rises, the calibration of the overvoltage detector 118 is checked to see that it trips at the proper threshold voltage. If it fails to trip, the system gate array returns a signal to the system monitor to show "Not OK" on the status indicator.

After the capacitor has been fully charged, the system gate array 56 sets the high voltage switch 110 to its normal initial discharge position (switches A and E closed, all other switches open) and commences discharge of the capacitor through the test and isolation relay 76 to the test load resistance $R_L$. $R_L$ simulates the load of a patient to whom the defibrillators electrodes may be attached. $R_L$ is preferably approximately 10 ohms, however, which is smaller than the minimum allowable patient resistance for the defibrillator. This low resistance assures that the test stresses all of the elements tested in the high current pathways for worst-case patient conditions.

During this part of the High Voltage Delivery self-test, the system gate array verifies overcurrent detection calibration by determining whether the CPU correctly identifies the overcurrent condition detected by current and charge measurement device 116. The system gate array also checks for proper operation of the charge threshold detector and that the overvoltage detector 118 trips properly when the capacitor voltage drops below the safe voltage threshold, in both cases by determining whether these events occur at their expected times. If either of these parameters is not its expected value, the system monitor displays "Not OK" on the status indicator.

As the capacitor voltage drops during discharge through the test load, the current measured by the current and charge measurement device 116 drops as well. The CPU marks the time the current drops below the overcurrent threshold ($t_0$). As the current continues to fall, the CPU marks the time ($t_1$) that the current reaches a value that is 37% of the overcurrent threshold. The difference of these two times is the time constant given by the product of the capacitor value C and the series resistance:

$$t_1 - t_0 = (R_L + R_{BITE}) * C.$$

Switch D is then closed to short out $R_{BITE}$. This results in another overcurrent situation, and the CPU once again marks the time ($t_2$) of capacitor decay to the overcurrent threshold and the time ($t_3$) to 37% of the threshold. Since $R_{BITE}$ has been removed, $$t_3 - t_2 = R_L * C.$$

Since the time measurements can be made very accurately, the relationships between the resistive and capacitive components (and therefore their calibration) can be verified very accurately as well:

$$\frac{t_1 - t_0}{t_3 - t_2} = \frac{R_L + R_{BITE}}{R_L}$$

$$C = \frac{t_3 - t_2}{R_L}$$

If the calculated resistance value differs from the expected value by more than a predetermined amount (e.g., 1%), or if the calculated capacitance value differs from the expected value by more than a predetermined amount (e.g., 5%), the system monitor displays the "Not OK" symbol.

In the preferred embodiment, the gain of the comparators of the current and charge measurement subsystems are determined by the particular values of the components used during assembly of the device. Due to allowable tolerance variation of the components, the times that the currents pass associated threshold values ($t_0$ and $t_2$) may vary from ideal values ($t_0$(ideal) and $t_2$(ideal)). Actual values of $t_0$ and $t_2$ are measured during self-test of the instrument and compared to stored $t_0$(ideal) and $t_2$(ideal). If the actual values of $t_0$ and $t_2$ measured during the High Voltage Discharge Test differ from the ideal values by less than a preset amount, then the gain on the comparator of the current and charge measurement device 116 is automatically recalibrated by the CPU to a range closer to the ideal value. If the actual values differ from the ideal by the preset amount or more, the test fails and the system monitor displays the "Not OK" symbol on the status indicator.

In a similar manner, the expected time for times for the measured charge delivery to cross the charge threshold used to determine first and second phase durations in normal operation is compared to the actual time. If the difference is less than a preset value, the CPU recalibrates the phase durations by recalculating the phase duration values according to a predetermined equation and storing the new values in the look-up table. Alternatively, the CPU could simply replace the original look-up table with another that is correlated with a particular time difference. If the time difference is equal to or greater than the preset value, then the test fails and the system monitor displays the "Not OK" symbol on the status indicator.

Another feature of the external defibrillator of preferred embodiment is an undercurrent detector. If the patient to whom the electrodes are attached has an impedance greater than a specified value, or if one of the electrodes has become dislodged or unattached, in normal operation the defibrillator's discharge will abort. This condition is detected by the current and charge measurement device 116 in conjunction with the CPU.

The High Voltage Delivery self-test verifies calibration of the undercurrent detector by determining whether the low current condition is detected as the capacitor continues its discharge and the discharge current falls. If the CPU fails to detect the undercurrent condition, the test fails and the system monitor displays the "Not OK" symbol on the status indicator.

After the capacitor has completely discharged, it is recharged and discharged through the second current path by opening all switches in high voltage switch 110, then closing switches B and C. Many of the same parameters described above can be measured to verify the functionality of switches B and C.

The Waveform Delivery self-test is performed only while the defibrillator is operating in normal mode (e.g., connected to a patient). The defibrillator evaluates the measured and calculated waveform parameters after each delivered shock to determine if the waveform was delivered as expected. For example, if the defibrillator is constructed and operated according to U.S. patent application Ser. No. 08/227,553 now U.S. Pat. No. 5,607,454, the defibrillator will analyze waveform parameters such as start voltage, phase 2 end voltage, phase 1 duration and phase 2 duration. If the delivered waveform parameters cannot be reconciled with other information available to the defibrillator, the defibrillator warns the operator of a potential fault condition by, e.g., displaying a warning on the defibrillator's LCD.

The three Calibration Standard self-tests are an automatic way of verifying that defibrillator system standards have not drifted out of calibration. The standards are the values of $R_L$, $R_{BITE}$, the system monitor clock, the CPU clock, the CPU A/D convertor reference voltage and the ECG front end A/D convertor reference voltage. For all test groupings except the run time test, the voltage references are checked against each other to determine if either has drifted far enough from its expected value to affect the accuracy of the defibrillator. Specifically, the analog reference voltage for the ECG front end A/D convertor (which has an expected value of 2.5 volts in the preferred embodiment) is measured by the CPU A/D convertor. If the measured digital value differs from 2.5 volts by more than a predetermined tolerance, then at least one of the two reference voltages (i.e., either the ECG front end A/D convertor reference voltage or the CPU A/D convertor reference voltage) has drifted so far so as to affect the reliability of the device.

The time references are cross-checked in a similar way. The CPU counts the clock pulses from the system monitor clock for a predetermined amount of time (as measured by the CPU clock). If the number of counted system monitor clock pulses differs from its expected value by more than a predetermined amount, then at least one of the two clocks has drifted out of the tolerance range.

In addition, as discussed above, the High Voltage Delivery self-test cross-checks the values of $R_L$ and $R_{BITE}$. Verification of the calibration of all three sets of reference variables is a prerequisite to the overcurrent detection calibration and charge threshold detection calibration described above.

In normal stand-by mode, the contacts beneath all buttons should be open. The Stuck Button self-test determines whether any of the contacts are closed. If so, the test returns a "Not OK" signal.

The remaining tests require user intervention and/or observation and are therefore part of only the BIT or POST test groupings. In the Button test, the user is prompted to depress identified buttons on the instrument to determine whether the buttons are functioning properly. All of the other tests run without user intervention. They each require the user to observe that the defibrillator elements tested are functioning correctly.

In addition to performing the self-tests according to the periodic schedule and in response to the battery insertion and operation of the defibrillator (as shown in FIG. 6), a group of self-tests can be performed automatically in response to environmental events, such as mechanical shock, e.g. as in a fall (as measured by an accelerometer); vibration (also as measured by an accelerometer); the invasion of moisture into the defibrillator housing (as measured by a humidity sensor); or exposure of the defibrillator to temperature extremes (as measured by a thermocouple, thermistor or other temperature sensor).

Variations of the structure and methods described above are within the scope of this invention. Tests and test structures may be tailored to meet the needs of a particular defibrillator design and its intended use environment.

What is claimed is:

1. An external defibrillator comprising:
    a high voltage delivery system comprising an energy source, an electrode interface and a switch connecting the energy source to the electrode interface;
    a controller operably connected to the high voltage delivery system; and
    a self-test system comprising a defibrillator status indicator, a test signal generator, and means for operating the defibrillator status indicator and the test signal generator prior to any attempted use of the defibrillator.

2. The defibrillator of claim 1 wherein the self-test system further comprises a functionality tester and communication channels between the functionality tester and the test signal generator and between the functionality tester and the status indicator.

3. The defibrillator of claim 2 wherein the self-test system further comprises a communication channel between the functionality tester and the switch.

4. The defibrillator of claim 2 wherein the self-test system further comprising a communication channel between the functionality tester and the controller.

5. The defibrillator of claim 2 wherein the self-test system further comprises a relay having an operational position and a test position, the self-test system further comprising a communication channel between the functionality tester and the relay.

6. The defibrillator of claim 1 wherein the self-test system further comprises a calibration verifier and communication channels between the calibration verifier and the test signal generator and between the calibration verifier and the status indicator.

7. The defibrillator of claim 6 further comprising an overcurrent detector, the self-test system further comprising a communication channel between the calibration verifier and the overcurrent detector.

8. The defibrillator of claim 6 further comprising an undercurrent detector, the self-test system further comprising a communication channel between the calibration verifier and the undercurrent detector.

9. The defibrillator of claim 6 further comprising an overvoltage detector, the self-test system further comprising a communication channel between the calibration verifier and the overvoltage detector.

10. The defibrillator of claim 6 further comprising an ECG front end, the self-test system further comprising a communication channel between the calibration verifier and the ECG front end.

11. The defibrillator of claim 6 wherein the high voltage delivery system comprises a resistor, the self-test system further comprising a communication channel between the calibration verifier and the resistor.

12. The defibrillator of claim 11 wherein the controller comprises means for using the high voltage delivery system resistor as a reference standard for the defibrillator.

13. The defibrillator of claim 11 further comprising a second resistor in communication with the controller, wherein the controller comprises means for using the high voltage delivery system resistor and the second resistor together as reference standards for the defibrillator.

14. The defibrillator of claim 6 wherein the high voltage delivery system comprises a capacitor, the self-test system further comprising a communication channel between the calibration verifier and the capacitor.

15. The defibrillator of claim 6 wherein the controller comprises a clock, the self-test system further comprising a communication channel between the calibration verifier and the clock.

16. The defibrillator of claim 15 wherein the controller comprises means for using the controller clock as a reference standard for the defibrillator.

17. The defibrillator of claim 16 further comprising a second clock in communication with the controller, wherein the controller comprises means for using the controller clock and the second clock together as reference standards for the defibrillator.

18. The defibrillator of claim 6 further comprising a reference voltage source, the self-test system further comprising a communication channel between the calibration verifier and the voltage source.

19. The defibrillator of claim 18 wherein the controller comprises means for using the reference voltage source as a reference standard for the defibrillator.

20. The defibrillator of claim 19 further comprising a second voltage source in communication with the controller, wherein the controller comprises means for using the first and second voltage sources together as reference standards for the defibrillator.

21. The defibrillator of claim 1 further comprising a battery, the self-test system further comprising a battery condition tester and communication channels between the battery condition tester and the battery, between the battery condition tester and the status indicator, and between the battery condition tester and the test signal generator.

22. The defibrillator of claim 1 wherein the test signal generator comprises a system monitor.

23. The defibrillator of claim 22 wherein the system monitor comprises an application specific integrated circuit.

24. The defibrillator of claim 22 further comprising a controller power supply, wherein the system monitor comprises a system monitor power supply separate from the controller power supply.

25. The defibrillator of claim 22 wherein the system monitor further comprises means for generating periodic test signals.

26. The defibrillator of claim 22 wherein the system monitor further comprises means for generating test signals in response to specified events or conditions.

27. The defibrillator of claim 26 further comprising means for receiving a removable battery and for connecting a battery to the high voltage delivery system, in which the event or condition is the insertion of a battery into the defibrillator.

28. The defibrillator of claim 22 in which the event or condition is environmental.

29. The defibrillator of claim 28 in which the environmental event or condition is temperature.

30. The defibrillator of claim 28 in which the environmental event or condition is moisture.

31. The defibrillator of claim 28 in which the environmental event or condition is mechanical shock.

32. The defibrillator of claim 28 which the environmental event or condition is vibration.

33. The defibrillator of claim 22 wherein the system monitor comprises a watchdog timer.

34. The defibrillator of claim 1 wherein the status indicator comprises a sound generator.

35. The defibrillator of claim 1 further comprising memory and a communication channel between the self-test system and the memory.

36. The defibrillator of claim 1 wherein the status indicator comprises a visual display.

37. The defibrillator of claim 36 in which the visual display comprises means for providing fail-safe operation.

38. A defibrillator comprising:
   a high voltage delivery system comprising an energy source and a switch connecting the energy source to the exterior of the defibrillator;
   a controller operably connected to the high voltage delivery system; and
   a self-test system comprising a defibrillator status indicator, a test signal generator, and a recalibrator.

39. The defibrillator of claim 38 further comprising a current sensor, the self-test system further comprising a communication channel between the recalibrator and the current sensor.

40. The defibrillator of claim 38 further comprising a waveform shape controller, the self-test system further comprising a communication channel between the recalibrator and the waveform shape controller.

41. An external defibrillator comprising:
   a high voltage delivery system comprising an energy source, an electrode interface and a switch connecting the energy source to the electrode interface;
   a controller operably connected to the high voltage delivery system; and
   a self-test system comprising a defibrillator status indicator, a periodic test signal generator, and means for operating the defibrillator status indicator and the periodic test signal generator prior to any attempted use of the defibrillator.

42. A method for automatically determining and indicating an operational status of an external defibrillator, the method comprising the following steps:
   generating a test signal within the external defibrillator automatically and periodically;
   performing a self-test in response to the test signal; and
   indicating the operational status of the defibrillator based on a result of the self-test;
   the generating, performing and indicating steps being performed prior to any attempted use of the defibrillator.

43. An external defibrillator comprising:
   a high-voltage delivery system; and
   a self-test system, the self-test system comprising a test signal generator and a fail-safe visual display.

44. A method for automatically determining and indicating an operational status of an external defibrillator, the method comprising the following steps:
   generating a test signal within the external defibrillator automatically in response to a predetermined event or condition;
   performing a self-test in response to the test signal; and
   indicating the operational status of the defibrillator based on a result of the self-test;
   the generating, performing and indicating steps being performed prior to any attempted use of the defibrillator.

45. The method of claim 44 wherein the step of generating a test signal within the defibrillator automatically in response to a predetermined event or condition comprises generating a test signal within the defibrillator automatically in response to insertion of a battery into the defibrillator.

46. The defibrillator of claim 44 in which the step of generating a test signal within the defibrillator automatically in response to a predetermined event or condition comprises generating a test signal within the defibrillator automatically in response to an environmental event or condition.

47. The method of claim 46 in which the step of generating a test signal within the defibrillator automatically in response to an environmental event or condition comprises generating a test signal within the defibrillator automatically in response to temperature.

48. The method of claim 46 in which the step of generating a test signal within the defibrillator automatically in response to an environmental event or condition comprises generating a test signal within the defibrillator automatically in response to moisture.

49. The method of claim 46 in which the step of generating a test signal within the defibrillator automatically in response to an environmental event or condition comprises generating a test signal within the defibrillator automatically in response to mechanical shock.

50. The method of claim 46 in which the step of generating a test signal within the defibrillator automatically in response to an environmental event or condition comprises generating a test signal within the defibrillator automatically in response to vibration.

51. The method of claim 44 wherein the step of performing a self-test comprises determining functionality of a defibrillator component or system.

52. The method of claim 44 wherein the step of performing a self-test comprises verifying calibration of a defibrillator component or system.

53. The method of claim 52 wherein the step of performing a self-test comprises performing a calibration verification self-test, the method further comprising the step of recalibrating a defibrillator component or system in response to the calibration verification self-test.

54. The method of claim 52 wherein the step of performing a self-test comprises discharging a capacitor and measuring electrical and time values associated with the capacitor's discharge.

55. The method of claim 52 wherein the step of performing a self-test comprises using a resistance within the defibrillator as a reference value.

56. The method of claim 52 wherein the step of performing a self-test comprises using two resistances within the defibrillator as reference values through a comparison of two resistance values.

57. The method of claim 52 wherein the step of performing a self-test comprises using a voltage source within the defibrillator as a reference value.

58. The method of claim 52 wherein the step of performing a self-test comprises using two voltage sources within the defibrillator as reference values through a comparison of two voltage source values.

59. The method of claim 52 wherein the step of performing a self-test comprises using a clock within the defibrillator as a reference value.

60. The method of claim 52 wherein the step of performing a self-test comprises using two clocks within the defibrillator as reference values through a comparison of two clocks.

61. The method of claim 44 wherein the indicating step comprises displaying status information on a visual display.

62. The method of claim 61 wherein the displaying step comprises providing an active display signal to the visual display, the visual display having a first state when provided with the active display signal and a second state when not provided with the active display signal, the second state indicating a nonoperational state of the defibrillator.

63. The method of claim 62 wherein the step of providing an active display signal comprises providing an AC signal.

64. The method of claim 44 wherein the indicating step comprises providing audible status information.

65. The method of claim 44 wherein the step of generating a test signal within the defibrillator automatically in response to a predetermined event or condition comprises generating a test signal within the defibrillator automatically in response to the passage of time.

66. The method of claim 44 wherein the step of performing a self-test comprises recalibrating a defibrillator component or system.

67. A method for testing and indicating an operational status of an external defibrillator comprising the following steps:

generating a test signal within the external defibrillator automatically and periodically;

performing a plurality of self-tests in response to the test signal to determine the operational status of a plurality of components of the defibrillator, the tests being performed without human intervention prior to any attempted use of the defibrillator; and indicating the operational status of the defibrillator in response to at least one of the self-tests.

68. The method of claim 67 wherein the generating step comprises generating a test signal within the defibrillator automatically on a predetermined schedule.

69. The method of claim 67 further comprising the step of generating a test signal within the defibrillator automatically in response to a predetermined event.

70. The method of claim 69 further comprising the step of generating a test signal within the defibrillator automatically in response to an environmental condition or event.

71. The method of claim 67 wherein the step of performing a plurality of self-tests comprises determining functionality of a defibrillator component or system.

72. The method of claim 71 wherein the step of performing a plurality of self-tests comprises verifying calibration of a defibrillator component or system.

73. The method of claim 72 further comprising the step of automatically recalibrating a defibrillator component or system in response to a self-test.

* * * * *

UNITED STATES PATENT AND TRADEMARK OFFICE
CERTIFICATE OF CORRECTION

PATENT NO. : 5,879,374
DATED : March 9, 1999
INVENTOR(S) : Powers et al.

It is certified that error appears in the above-identified patent and that said Letters Patent is hereby corrected as shown below:

Column 1, (line 9), after "abandoned" insert --,--.

Column 10, (line 38), delete "553now" and insert therefor --553 now--.

Column 10, (line 39), after "preferred" insert --external--.

Column 10, (line 67), delete "5,697,454" and insert therefor --5,607,454--.

IN THE CLAIMS

Column 15, (line 54), delete "22" and insert therefor --26--.

Signed and Sealed this

Seventeenth Day of August, 1999

Attest:

Q. TODD DICKINSON

*Attesting Officer*                *Acting Commissioner of Patents and Trademarks*

(12) EX PARTE REEXAMINATION CERTIFICATE (10888th)
United States Patent
Powers et al.

(10) Number: US 5,879,374 C1
(45) Certificate Issued: Jun. 16, 2016

(54) EXTERNAL DEFIBRILLATOR WITH AUTOMATIC SELF-TESTING PRIOR TO USE

(75) Inventors: Daniel J. Powers, Bainbridge Island, WA (US); David Cameron, Seattle, WA (US); Clinton S. Cole, Seattle, WA (US); Thomas D. Lyster, Bothell, WA (US); Steven T. Mydynski, Bothell, WA (US); Carlton B. Morgan, Bainbridge Island, WA (US)

(73) Assignee: PHILIPS ELECTRONICS NORTH AMERICA CORPORATION, Andover, MA (US)

Reexamination Request:
No. 90/013,373, Oct. 27, 2014
No. 90/013,401, Nov. 17, 2014

Reexamination Certificate for:
Patent No.: 5,879,374
Issued: Mar. 9, 1999
Appl. No.: 08/240,272
Filed: May 10, 1994

Certificate of Correction issued Aug. 17, 1999

Related U.S. Application Data

(63) Continuation-in-part of application No. 08/063,631, filed on May 18, 1993, now abandoned.

(51) Int. Cl.
*A61N 1/39* (2006.01)

(52) U.S. Cl.
CPC .................... *A61N 1/3931* (2013.01)

(58) Field of Classification Search
None
See application file for complete search history.

(56) References Cited

To view the complete listing of prior art documents cited during the proceedings for Reexamination Control Numbers 90/013,373 and 90/013,401, please refer to the USPTO's public Patent Application Information Retrieval (PAIR) system under the Display References tab.

*Primary Examiner* — Charles Craver (57) ABSTRACT

A defibrillator with an automatic self-test system that includes a test signal generator and a defibrillator status indicator. The test system preferably performs functional tests and calibration verification tests automatically in response to test signals generated periodically and/or in response to predetermined conditions or events and indicates the test results visually and audibly. The invention also relates to a method for automatically determining and indicating a defibrillator's status without human intervention.

**Attention is directed to the decision of *Koninklijke Philips Electronics N.V. et al v. Zoll Medical Corporation* (1:10cv11041); *Koninklijke Philips Electronics N.V. et al v. Access Cardiosystems Inc* (2:03cv1318); *Koninklijke Philips Electronics N.V. et al v. Defibtech L.L.C. et al* (2:03cv1322); *Koninklijke Philips Electronics N.V. et al v. Cardiac Science Inc* (2:03cv1324) relating to this patent. This reexamination may not have resolved all questions raised by these decisions. See 37 CFR 1.552(c) for *ex parte* reexamination and 37 CFR 1.906(c) for *inter partes* reexamination.**

At the time of issuance and publication of this certificate, the patent remains subject to pending reexamination control number 90/013,680 filed Jan. 8, 2016. The claim content of the patent may be subsequently revised if a reexamination certificate issues from the reexamination proceeding.

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 42, 43, 67 and 68 is confirmed.

Claims 1-41, 44-66 and 69-73 were not reexamined.

\* \* \* \* \*